United States Patent [19]

Gittos

[11] Patent Number: 4,906,755

[45] Date of Patent: Mar. 6, 1990

[54] ESTERS OF HEXAHYDRO-8-HYDROXY-2,6-METHANO-2H-QUINOLIZIN-3-(4H)-ONE AND RELATED COMPOUNDS

[75] Inventor: Maurice W. Gittos, Plobsheim, France

[73] Assignee: Merrell Dow Pharmaceuticals Inc., Cincinnati, Ohio

[21] Appl. No.: 376,172

[22] Filed: Jun. 30, 1989

Related U.S. Application Data

[63] Continuation of Ser. No. 185,631, Apr. 26, 1988, abandoned, which is a continuation-in-part of Ser. No. 926,619, Nov. 3, 1986, abandoned.

[51] Int. Cl.$^4$ ............................................. C07D 453/00
[52] U.S. Cl. ......................................... 546/94; 546/72; 544/126
[58] Field of Search ................ 546/72, 94; 544/126

[56] References Cited

U.S. PATENT DOCUMENTS

| | | | |
|---|---|---|---|
| 4,563,465 | 1/1986 | Fozard | 514/304 |
| 4,585,866 | 4/1986 | Fozard | 435/129 |
| 4,713,380 | 12/1987 | Masyanoff | 546/84 |

FOREIGN PATENT DOCUMENTS

| | | | |
|---|---|---|---|
| 1187502 | 5/1985 | Canada | 260/292.7 |
| 2131420 | 1/1986 | United Kingdom | 451/12 |
| 2132189 | 2/1986 | United Kingdom | 451/12 |
| 2125398 | 11/1986 | United Kingdom | 451/12 |

OTHER PUBLICATIONS

Mar. J., Adv. Org. Chem. 2nd Ed. p. 363–365.
W. Schneider, et al., *Archiv Der Pharmazie*, 309, 447–457 (1976).
W. Schneider, et al., *Tetrahedron Letters*, 15, 1583–1586 (1966).
W. Schneider, et al., *Archiv Der Pharmazie*, 308, 365–375 (1975).
P. G. Sammes, et al., *Journal of the Chemical Society, Chemical Communications*, 1, 367–368 (1976).
B. Maurer, et al., *Helvetica Chemica Acta*, 59, 1169–1185 (1976).
P. Fludzinski, et al., *J. Med. Chem.*, 30(9), 1535–1537 (1987).

*Primary Examiner*—Mary C. Lee
*Assistant Examiner*—J. Richter
*Attorney, Agent, or Firm*—John J. Kolano

[57] ABSTRACT

The present invention is directed to a group of esters of hexahydro-8-hydroxy-2,6-methano-2H-quinolizin-3(3H)-ones and related compounds. The compounds are prepared from the appropriate carboxylic acids and alcohols by standard procedures or, where steric factors are significant, a new process which makes use of heavy metal salts of super acids can be used. The compounds involved are useful in the treatment of migraine and similar disorders and in cytotoxic drug-induced vomiting.

10 Claims, No Drawings

ESTERS OF HEXAHYDRO-8-HYDROXY-2,6-METHANO-2H-QUINOLIZIN-3-(4H)-ONE AND RELATED COMPOUNDS

This is a continuation of application Ser. No. 185,631, filed Apr. 26, 1988, which is a continuation-in-part of application Ser. No. 926,619, filed Nov. 3,1986 now abandoned.

The present invention is directed to esters of hexahydro-8-hydroxy-2,6-methano-2H-quinolizin-3(4H)-one and hexahydro-8-hydroxy-2,6-methano-2H-quinolizines with certain aromatic and heterocyclic carboxylic acids. The invention is also directed to novel polycyclic alcohols which serve as intermediates in the preparation of the esters of this invention and also to a novel process for preparing a group of esters of the present invention.

More particularly, the present invention is directed to compounds of the formula:

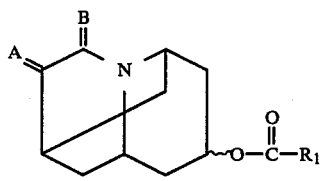

wherein A is $=H_2$, $=O$, $=(H)(OH)$ or $=N-OH$; B is $=H_2$, $=(H)(CH_3)$, $=(H)(CH_2NR_3R_4)$ or $=CH_2$ wherein $R_3$ and $R_4$ are $C_{2-4}$ alkyl or are combined to give tetramethylene, pentamethylene or $-CH_2CH_2-O-CH_2CH_2-$; $R_1$ is

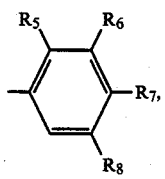

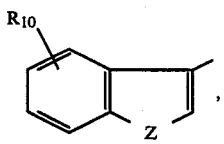

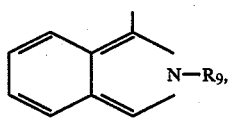

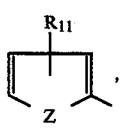

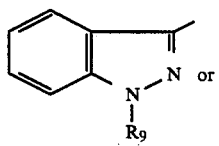 or

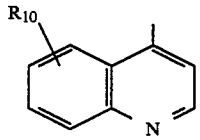

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, $(C_{1-4}$ alkyl)amino, $(C_{1-4}$ alkyl)$_2$amino, $C_{1-3}$ alkoxy or nitro; $R_9$ is hydrogen, $C_{1-4}$ alkyl or phenyl$(C_{1-2}$ alkyl); $R_{10}$ is hydrogen, halogen, $C_{1-4}$ alkyl, $C_{1-4}$ alkoxy, hydroxy, cyano or $-CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quaternary ammonium salts of the aforesaid compounds.

Examples of the $C_{1-4}$ alkyl groups referred to above are methyl, ethyl, propyl, isopropyl and butyl. Examples of the $C_{1-4}$ alkoxy groups are methoxy, ethoxy and propoxy, with butoxy being an additional example when the alkoxy is $C_{1-4}$. The halogens referred to above can be fluorine, chlorine or bromine. When the wavy line in the general structural formula is changed to a solid line, this indicates that the configuration of the compounds is endo. Such endo-compounds can also be referred to as trans. Similarly, exo-compounds can also be referred to as cis. Any hydrates of the present compounds are considered as equivalent to the compounds themselves and this would include compounds in which the carbonyl (i.e., A is $=O$) exists as $=(OH)_2$.

A preferred group of compounds are those wherein the ester is attached to the polycyclic ring in the endoconfiguration. A further preferred group are those having the endo-configuration wherein A is $=O$ and $=(OH)_2$. In a still further preferred group, B is additionally $=H_2$.

The pharmaceutically acceptable acid addition salts referred to above can be non-toxic salts with suitable acids such as those with inorganic acids, for example, hydrochloric, hydrobromic, nitric, sulfuric or phosphoric acids; or with organic acids such as organic carboxylic acids, for example, acetic, propionic, glycolic, maleic, hydroxymaleic, malic, tartaric, citric, salicylic, 2-acetyloxybenzoic, nicotinic or isonicotinic; or organic sulfonic acids, for example methanesulfonic, ethanesulfonic, 2-hydroxyethanesulfonic, 4-toluenesulfonic or 2-naphthalenesulfonic. Quaternary ammonium salts are formed with alkyl halides such as methyl chloride, methyl bromide, methyl iodide or ethyl bromide; or with sulfate esters such as methyl 4-toluenesulfonate or methyl 2-naphthalenesulfonate.

Some specific examples of compounds encompassed by the present invention are the following:
endo-8-(3,5-Dimethylbenzoyloxy)hexahydro-2,6-methano-2H-quinolizin-3(4H)-one
exo-8-(3,5-Dimethylbenzoyloxy)hexahydro-2,6-methano-2H-quinolizin-3(4H)-one
endo-8-(3,5-Dichlorobenzoyloxy)hexahydro-2,6-methano-2H-quinolizin-3(4H)-one
endo-8-(3,5-Dimethoxybenzoyloxy)hexahydro-2,6-methano-2H-quinolizin-3(4H)-one
endo-8-(4-Aminobenzoyloxy)hexahydro-2,6-methano-2H-quinolizin-3(4H)-one
endo-8-(4-Dimethylaminobenzoyloxy)hexahydro-2,6-methano-2H-quinolizin-3(4H)-one endo-8-(3,5-Dimethylbenzoyloxy)octahydro-2,6-methano-2H-quinolizine endo-8-(3-Indolylcarbonyloxy)octahydro-2,6-methano-2H-quinolizine endo-8(5-Cyano-3-indolylcarbonyloxy)hexahydro-2,6-methano2H-quinolizin-3(4H)-one endo-8-(3,5-Dichlorobenzoyloxy)hexahydro-2,6-methano-4methyl-2H-quinolizin-3(4H)-one endo-8-(3-Indolylcarbonyloxy)hexahydro-4-(diethylaminomethyl)-2,6-methano-2H-quinolizin-3(4H)-one endo-8-(3-Indolylcarbonyloxy)-3-hydroxyimino-2,6-methanooctahydro-2H-quinolizine endo-8-(2-Methyl-1-isoindolycarbonyloxy)hexahydro-2,6methano-2H-quinolizin-3(4H)-one endo-8-(2-Pyrrolidinylcarbonyloxy)hexahydro-2,6-methano-2H-quinolizin-3(4H)-one endo-8-(3-Indolylcarbonyloxy)-2,6-methanooctahydro-2H-quinolizin-3-ol endo-Hexahydro-8-(1-methyl-3-indazolylcarbonyloxy)-2,6-methano-2H-quinolizin-3(4H)-one endo-Hexahydro-8-(3-indazolylcarbonyloxy)-2,6-methano-2H-quinolizin-3(4H)-one The compounds of the present invention can be prepared by reacting an alcohol or a reactive derivatives thereof, said alcohol having the formula

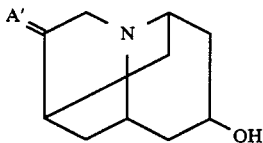

wherein A' is =O or =H₂, with a reactive equivalent of an acid of the formula:

R₁COOH wherein R₁ is defined as above. By a reactive equivalent of the acid is meant the corresponding acid chloride or bromide or the corresponding glyoxylyl chloride or bromide or the carboxylic acid imidazole obtained by the reaction of the appropriate acid halide with N,N-carbonyldiimidazole; or any similar acid derivative which would yield the simple carboxylic acid ester on reaction with an alcohol or with a reactive derivative of an alcohol. More specifically, where the —OH in the alcohol is equatorial (exo), then it can be reacted with the appropriate carboxylic acid imidazole obtained by the reaction of the acid halide with N,N-carbonyldiimidazole. Alternatively, the acid can be converted to the acid chloride by standard procedures (e.g., thionyl chloride) and then reacted with the alcohol or an alkali metal salt of the alcohol such as the lithium salt obtained by the reaction of lithium hydride with the alcohol in tetrahydrofuran.

When the —OH group in the starting alcohol is axial (endo), it can also be converted to the corresponding ester by reaction with the appropriate acid chloride or bromide with the reaction being carried out in the presence of an equivalent of a suitable tertiary base such as 4-dimethylaminopyridine in a high boiling inert solvent such as xylene. In this case, however, long heating (24–84 hours) at a temperature at or above 140° C. is necessary so that the procedure would not be suitable for use with acid halides that are not stable under the indicated conditions. Thus, it was necessary to use an alternative procedure for the preparation of such compounds. In this procedure, an appropriate acid chloride or bromide or a glyoxylyl chloride or bromide, in a nitroparaffin solvent, is reacted with a solution of a super acid salt of the alcohol and an equivalent amount of a heavy metal salt of the same super acid. The glyoxylyl chloride can be used in the process as indicated because it decarbonylates readily under the conditions used. The reaction itself can be carried out over a period of 1–24 hours at temperatures ranging from −80° C. to ambient temperatures (about 23° C.). Examples of suitable super acids with M =H are MBF₄, MAsF₆, MSbF₆, MPF₆, MTaF₆ or MNbF₆ with examples of suitable heavy metals (M) being silver and thallium. Examples of nitroparaffin solvents are nitromethane, nitroethane, 1-nitropropane and 2-nitropropane.

Actually, where the group R1 contains a primary or secondary amino group, it is usually protected during the above reaction, with a benzyl group being commonly used to protect a secondary amine and a benzyloxycarbonyl group being used to protect a primary amine. In either case, the protecting group in the product is removed by conventional procedures, for example by hydrogenation with hydrogen and a palladium catalyst.

Various procedures can be used to convert those compounds wherein A is =O and whose preparation is described below, to other different bridged derivatives of the present invention by standard methods. Thus, the ketone group in the polycyclic system can be reduced to the corresponding alcohol using an alkali metal (sodium or potassium) borohydride in a lower alkanol such as methanol or ethanol.

The ketone group can also be reduced completely to a methylene group by a two step procedure. In the first step, the ketone is reacted with ethylene dithiol or trimethylene dithiol in the presence of a strong acid such as hydrochloric acid or BF₃ to give the corresponding dithioketal. The reaction is carried out in a suitable polar solvent such as nitromethane or acetic acid. The dihioketal is then reduced with hydrazine in the presence of Raney nickel in a lower alkanol solvent such a 2-propanol at elevated temperatures (60–100° C.). Actually this same procedure can be used to reduce the original starting alcohol, hexahydro-8-hydroxy-2,6-methano-2H-quinolizin-3(4H)-one, to 8-hydroxy-2,6-methanooctahydro-2H-quinolizine which can itself be reacted with acid derivatives as described earlier to give the corresponding esters.

Compounds containing other B-groups (i.e. aminomethyl, methylene or methyl groups) can be obtained from products in which A is =O and =B is H₂ by a Mannich reaction using formaldehyde and a secondary amine such as dimethylamine, diethylamine, piperidine or pyrrolidine. This reaction gives the corresponding aminomethyl compound and, when B is dimethylaminomethyl, the amino moiety is eliminated on heating at 90–110° C. in an inert solvent such as toluene to give the corresponding methylene compound (B is =CH₂). This exocyclic methylene compound can be isolated by standard methods and transformed into a methyl group by hydrogenation, for example, by using hydrogen and platinum oxide.

To obtain those compounds in which A is hydroxyimino (=N—OH), the ketone referred to above can be reacted with hydroxylamine hydrochloride by standard procedures.

The alcohol used as a reactant in the above procedure can be obtained from known alkyl (C₁₋₄) 3-cyclopentene-1carboxylates by a multi-step procedure. Specifically, the double bond in the indicated cyclopentene is oxidized to a 1,2-diol using N-methylmorpholine N-oxide in the presence of osmium tetroxide catalyst. The diol is then cleaved to the corresponding dialdehyde using sodium metaperiodate. A Robinson-Schopf cyclization of the dialdehyde with a lower alkyl glycine ester and acetone-dicarboxylic acid, preferably at pH 4, gives a pseudopelletierine derivative of the following type:

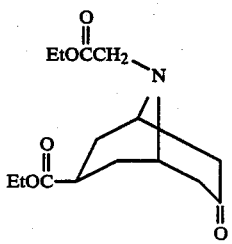

The ketone group is reduced to an alcohol using sodium borohydride and the product is reacted with dihydropyran to protect the —OH group as a tetrahydropyranyl ether. Dieckmann cyclization of the diester using a strong base (e.g. potassium t-butoxide) followed by aqueous acid hydrolysis and decarboxylation gives the desired alcohol. The resulting alcohols can exist in two conformations - axial and equatorial. The main product obtained by the above procedure is the axial alcohol and it can be separated from the equatorial isomer by crystallization of the camphorsulfonate or tetrafluoroborate salt.

The present compounds are useful for the treatment of pain, especially migraine, vascular and cluster headaches and trigeminal neuralgia. They are also useful in the treatment of nausea and vomiting arising from treatment with cancer chemotherapeutic agents.

In the past, acute attacks of migraine have been treated with a peripheral vasoconstrictor, such as ergotamine, which may be co-administered with caffeine, and dihydroergotamine; an antipyretic analgesic, such as acetylsalicylic acid or p-acetylaminophenol; and/or an antiemetic such as cyclizine, metoclopramide and thiethylperazine. It has also been reported (J. B. Hughes, Med. J. Aust. 2, No. 17, 580 (1977)) that immediate relief of an acute migraine attack can be obtained by slow intravenous injection of metoclopramide (10 mg).

It is believed that 5-hydroxytryptamine (5-HT) is the naturally occurring substance most likely to play a role in the pathophysiology of migraine. Increased amounts of 5-HT and it metabolite 5-hydroxyindoleacetic acid are excreted in the urine during most attacks. Further, plasma and platelet 5-HT concentrations fall rapidly at the onset of an attack and remain low while the headache persists. Moreover, attacks of migraine have been clearly associated with periods of thrombocytopaenia in certain patients. It has been proposed that compounds which block the activity of 5-HT would be of use in the symptomatic treatment of migraine (J. R. Fozard, International Headache Congress 1980, reported in *Advances in Neurology*, Vol 33., Raven Press, New York, 1982).

The known migraine prophylactic drugs, methysergide, propranolol, amitriptyline, and chlorpromazine have widely different pharmacological activities but all are 5-HT D-receptor antagonists at the doses used clinically for the prophylaxis of migraine. Metoclopramide is a potent 5-HT M-receptor antagonist and it has been proposed (J. R. Fozard supra) that a blockade of the M-receptor present on afferent sensory neurones affords symptomatic relief in an acute migraine attack.

The potency as 5-HT receptor antagonists of (—) cocaine and some related compounds, including pseudotropyl benzoate (i.e., benzoylpseudotropine) and 3,5-dichlorobenzoyltropine has been reported (J. R. Fozard et al., *Eur. J. Pharmacol.*, 59, (1979) 195–210; J. R. Fozard, *Naunyn-Schmiedeberg's Arch Pharmacol.*, 326, (1984), 36–44). The $pA_2$ values reported for metoclopramide, pseudotropyl benzoate, nor (—) cocaine and benzoyltropine are 7.2, 7.0, 7.7, and 7.2 respectively whilst the $pA_2$ value determined for 3,5-dichlorobenzoyltropine by the same procedure is 9.3 (J. R. Fozard et al., *Eur. J. Pharmacol.*, 49, (1978) 109–112; J. R. Fozard, *NaunynSchmiedeberg's Arch Pharmacol.*, 326, (1984), 36–44). In a double-blind clinical trial, 3,5-dichlorobenzoyltropine proved an effective treatment for the acute migraine attack (C. Loisy et al., *Cephalalgia*, 5, (1985) 79–82). A further series of tropine esters, with $pA_2$ values for blockade of the 5-HT M-receptors between 7.7 and 13.6 have been described by Richardson et al., *Nature*, 316, (1985) 26–131.

The compounds of the present invention block the M-receptors for 5-hydroxytryptamine (5-HT) on afferent sensory neurones, certain of which subserve the transmission of pain. As explained above, the blocking of such M-receptors appears to be a mechanism whereby the symptoms of migraine can be relieved. Accordingly, the present compounds are useful in the treatment of migraine when administered in amounts sufficient to effectively block the said M-receptors.

In addition, compounds blocking 5-HT M-receptors, including metoclopramide, 3,5-dichlorobenzoyltropine and (3α-tropanyl)-1H-indole-3-carboxylic acid ester, are highly effective in preventing the nausea and vomiting induced by cancer chemotherapeutic agents in an animal experimental model (W. D. Miner et al., *Brit. J. Pharmacol.*, 88, (1986) 374; W. D. Miner and G. J. Sanger, *Brit J. Pharmacol.*, 88, (1986) 497–499; B. Costall et al., *Neuropharmacology*, 25, (1986) 959–961). It is believed that cytotoxic drug-induced vomiting involves a 5-HT M-receptor mechanism (W. D. Miner and G. J. Sanger, *Brit J. Pharmacol.*, 88, (1986) 497–499). Accordingly, the present compounds are useful in the treatment of cytotoxic drug-induced vomiting when administered in amounts sufficient to effectively block the said M-receptors.

The activity of the compounds against 5-HT can be assessed by determining their $pA_2$ values in the isolated rabbit heart as described by J. R. Fozard et al., *Eur. J. Pharmacol.*, 59, 195–210 (1979). In the method described, the molar concentration of antagonist which reduces the effects of twice the $ED_{50}$ of 5-HT to that of the $ED_{50}$ in the absence of antagonist is determined. The $pA_2$ value is the negative logarithm of said molar concentrations. In general terms, the higher the $pA_2$ value the more potent is the compound. When tested in this way, the present compounds show $pA_2$'s generally in the range of about 8 to 10.

The activity of these compounds against 5-HT can be assessed in vivo by measurement of the effect of the compound on the Von Bezold-Jarisch Reflex induced by 5-HT injected intravenously into the rat (see Paintal A. S., *Physiol. Rev.*, 53, 159–227 (973); J. R. Fozard, *Naunyn-Schmiedeberg's Arch. Pharmacol.*, 326, (1984) 36–44). The transient cardiac slowing arises from an increased afferent vagus activity arising from stimulation by 5-HT of sensory afferent fibers in and around the heart. When tested against the Von Bezold-Jarisch Reflex induced by 5-HT, compounds endo-8-(3,5-dimethylbenzoyloxy)hexahydro-2,6-methano-2H-quinolizin-3(4H)-one hydrochloride and endo-hexahydro-8-(3-indolylcarbonyloxy)-2,6-methano-2H-quinolizin-3(4H)one hydrochloride suppressed the response dose-dependently at doses of 0.01–0.1 mg/kg given intravenously or 0.25–1 mg/kg given orally.

The present compounds appear to be highly selective in their action against the 5-HT M-receptor. Their potency against other 5-HT receptors and other spasmogens, in particular carbachol, phenylephrine, histamine and calcium, is known to be at least three orders lower that against 5-HT M-receptors. Accordingly, their use in the treatment of migraine or cytotoxic drug-induced vomiting should be without any side effects.

The present compounds can be administered in various manners to achieve the desired effect. The compounds can be administered alone or in the form of pharmaceutical preparations to the patient being treated either orally or parenterally, for example, subcutaneously or intravenously. They can also be administered by inhalation or by suppository. The amount of compound administered will vary and can be any effective migraine-relieving amount or amount effective in cytotoxic drug vomiting. Depending upon the patient and the mode of administration, the quantity of compound administered may vary over a wide range to provide from about 0.01 mg/kg to about 10 mg/kg, usually 0.03 to 3.0 mg/kg, of body weight of the patient per dose. Unit doses of these compounds can contain, for example, from about 0.5 mg to 100 mg, usually 1 to 50 mg and preferably 3 to 30 mg, of the compound and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

Specific formulations of the present invention are prepared in a manner well known per se in the pharmaceutical art and usually comprise one or more active compounds of the invention in admixture or otherwise in association with a pharmaceutically acceptable carrier or diluent therefor. The active ingredient will usually be mixed with a carrier, or diluted by a diluent, or enclosed or encapsulated in a capsule, sachet, cachet, paper or other container. A carrier or diluent may be solid, semisolid or liquid material which serves as a vehicle, excipient or medium for the active ingredient. Suitable carriers or diluents are well known per se. See Remington's Pharmaceutical Sciences, Mack Publishing Company, Easton, Pennsylvania, for a description of the preparation of such formulations.

The formulations of the invention may be adapted for enteral or parenteral use and may be administered to the patient in the form of tablets, capsules, suppositories, solutions, suspensions or the like.

The compounds of the present invention can be used in migraine therapy in combination with other antimigraine drugs having different modes of action. Such drugs include those used prophylactically, such as barbiturates, diazepam, chlorpromazine, amitriptyline, propranolol, methysergide, pizotifen, cyproheptadine, dihydroergotamine, and clonidine, and those used in the acute attack, such as vasoconstrictor agents, e.g., ergotamine and dihydroergotamine, analgesic/ anti-inflammatory agents, e.g., aspirin, paracetamol and indomethacin, or antinauseants, e.g., cyclizine, metoclopramide, and thiethylperazine (see J. F. Fozard, *J. Pharm. Pharmaco.*, 27, 297–321 (1975); J. R. Saper, *J. Amer. Med. Assoc.*, 239, 480–484 (1978); J. R. Fozard, supra). As an example, compounds of the present invention would be beneficial in combination with aspirin 300–1200 mg or methysergide 2–6 mg given daily.

The following examples are presented to illustrate the compounds used in the present invention, but they should not be construed as limiting it in any way.

EXAMPLE 1

To a stirred solution of 160 g of diethyl malonate in 1.5 l of dry dimethylformamide at 0° C. under nitrogen was slowly added 30 g of lithium hydride. After the evolution of hydrogen ceased (2 hours) 143 g of cis-1,4-dichloro-2-butene was slowly added and the mixture allowed to come to room temperature. After 72 hours, the mixture was diluted with a mixture of ether and hexane (1:4) and poured into water. The organic layer was washed with water and brine before drying over magnesium sulfate. Distillation gave diethyl 3-cyclopentene-1,1-dicarboxylate, bp 70–80° C./0.1 mm, containing a small amount (~10%) of diethyl 2-vinylcyclopropane-1,1-dicarboxylate.

The impure cyclopentene diester (148.5 g) obtained above was added to a solution of 118 g of potassium hydroxide in 1333 ml of 80% ethanol and the stirred solution warmed at 60–70° C. overnight. The ethanol was evaporated and the residue treated with an ice cold solution of concentrated sulphuric acid (107 ml) in water (274 ml). Extraction of the acid mixture with ether (3×400 ml) followed by evaporation of the dried ether extracts gave a residue of the diacid which was decarboxylated to the monoacid by heating in an oil bath at 170–180° C. for 1 hour. The residual oil was distilled to give crude 3-cyclopentene-1-carboxylic acid, bp 68–73° C. (1 mm) containing some γ-vinyl-γ-butyrolactone. A solution of 98 g of potassium carbonate in 300 ml of water was added and the mixture extracted with ether to remove the γ-vinyl-γ-butyrolactone. Acidification of the aqueous solution and extraction with ether afforded pure 3-cyclopentene-1-carboxylic acid.

EXAMPLE 2

A mixture of 52 g of 3-cyclopentene-1-carboxylic acid and excess thionyl chloride was stirred at room temperature for 1 hour. The excess thionyl chloride was evaporated and the residue distilled to give 3-cyclopentene-1-carbonyl chloride, bp 52–58° C.

The acid chloride obtained above was slowly added to an ice cooled stirred solution of 32 g of pyridine in 150 ml of ethanol. The mixture was stirred for a further hour, the ethanol evaporated and the residue treated with water and ether. The ether layer was separated, washed several times with water and dried. Evaporation of the ether left a residue of ethyl 3-cyclopentene-1-carboxylate, bp 62.5–66° C./14 mm.

EXAMPLE 3

A solution containing 84.6 g of N-methylmorpholine N-oxide, 1 g of osmium tetroxide, 230 ml of water and 115 ml of acetone was allowed to stir for 30 minutes at room temperature. To this stirred mixture was added, very slowly over at least 8 hours, a solution of 80 g of ethyl 3-cyclopentene-1-carboxylate in 115 ml of acetone. The stirred mixture was heated at 50° C. for 2 hours to complete the reaction (verified by TLC examination using ethyl acetate/hexane 70/30). Sodium bisulfite (~10 g) was added, the stirring continued for a further 15 minutes, and the mixture filtered through Celite. The pH of the filtrate was adjusted to 7 by the addition of 12 N sulfuric acid (37 ml), the acetone evaporated, the pH of the residual solution adjusted to 2 with 12 N sulfuric acid (13 ml) and the solution extracted with ethyl acetate (4×250 ml). Evaporation of the dried ethyl acetate solution gave 4-ethoxycarbonyl-1,2-cyclopentanediol.

EXAMPLE 4

A solution of 85.4 g of sodium periodate in 500 ml of water was slowly added to a stirred solution of 69 g of 4-ethoxycarbonyl-1,2-cyclopentanediol in 690 ml of tetrahydrofuran. The reaction was exothermic and cooling was necessary. After two hours a precipitate of sodium iodate was filtered off and the solution concentrated at room temperature to remove most of the tetrahydrofuran. The resulting aqueous solution contained the desired β-ethoxycarbonylglutaraldehyde and was used directly in the next reaction.

To a stirred suspension of 400 g of potassium hydrogen phthalate in 800 ml of water was added, in sequence, a solution of 80 g of acetonedicarboxylic acid in 1200 ml of water, a solution of 80 g of glycine ethyl ester hydrochloride in 400 ml of water, and finally the solution of β-ethoxycarbonylglutaraldehyde obtained above. The mixture was stirred for 20 hours at room temperature during which time carbon dioxide evolved. The mixture was basified by the addition of an excess of aqueous potassium carbonate and extracted with ethyl acetate several times. Evaporation of the dried ethyl acetate extracts gave a syrup consisting mainly of 7-ethoxycarbonyl-9-(ethoxycarbonylmethyl)-9-azabicyclo-[3.3.1]nonan-3-one.

EXAMPLE 5

Sodium borohydride (17 g) was added in small portions to a stirred solution of 87.6 g of 7-ethoxycarbonyl-9-(ethoxy- carbonylmethyl)-9-azabicyclo[3.3.1]nonan-3-one in 750 ml of ethanol. The mixture was stirred overnight at room temperature, the ethanol evaporated and the residue treated with 200 ml of water. Hydrochloric acid (2 M) was added until the mixture was acid and this acid solution was immediately basified by the addition of saturated potassium carbonate solution. Extraction with ethyl acetate and evaporation of the dried extract gave a syrup which consisted mainly of 7-ethoxycarbonyl-9-(ethoxycarbonylmethyl)-9-azabicyclo[3.3.1]nonan-3-ol. The syrup can be purified by column chromatography using silica and elution with hexane-ethyl acetate (30:70).

EXAMPLE 6

A solution of 26.1 g of the crude 7-ethoxycarbonyl-9-(ethoxycarbonylmethyl)-9-azabicyclo[3.3.1]nonan-3-ol in 250 ml of methylene chloride was treated with one equivalent of methanesulfonic acid (8.42 g). The methylene chloride solution was concentrated to about 35 ml, 9.5 ml of dihydropyran was added together with one drop of methanesulfonic acid, and the mixture stirred for 3 hours at room temperature. The mixture was then poured into saturated potassium carbonate solution and the product separated by extraction with ethyl acetate.

Evaporation of the dried ethyl acetate extracts gave a syrup consisting mainly of the tetrahydropyranyl ether of 7-ethoxycarbonyl-9-(ethoxycarbonylmethyl)-9-azabicyclo[3.3.1]nonan-3-ol. It can be purified by column chromatography using silica and elution with hexane-ethyl acetate (20:80), Rf 0.7.

EXAMPLE 7

A solution of 34 g of the tetrahydropyranyl ether of 7-ethoxycarbonyl-9-(ethoxycarbonylmethyl)-9-azabicyclo[3.3.1]nonan-3-ol in 800 ml of anhydrous toluene was treated with 19 g of potassium tert-butoxide and the stirred mixture heated at 100° C. for 2 hours. Anhydrous formic acid (7.85 g) was added to the cooled mixture, the potassium formate was filtered off, and the toluene solution evaporated to give a syrup. The syrup was treated with 300 ml of 5 N hydrochloric acid and the stirred solution refluxed overnight. The cooled mixture was clarified by an extraction with methylene chloride and the aqueous acid solution evaporated to dryness. The residue was dissolved in a little water and the solution treated with a large excess of saturated potassium carbonate solution. Extraction of the resulting mixture with ethyl acetate and evaporation of the dried ethyl acetate solution gave endo-hexahydro-8-hydroxy-2,6-methano-2H-quinolizin-3(4H)-one as an oil which crystallized on standing. The base was converted to its camphorsulfonate salt, m.p. 178° C., using one equivalent of camphorsulfonic acid in ethanol.

EXAMPLE 8

A mixture of 1.8 g of endo-hexahydro-8-hydroxy-2,6-methano-2H-quinolizin-3(4H)-one, hydrofluoroboric acid (0.88 g; 60% aqueous solution) and 20 ml of ethanol was evaporated, the residue was treated with 50 ml of anhydrous toluene, and the mixture again evaporated. A stirred suspension of the anhydrous residue in 50 ml of anhydrous nitroethane at −78° C. was treated with 1.94 g of anhydrous silver tetrafluoroborate and a solution of 1.7 g of 3,5-dimethylbenzoyl chloride in 20 ml of anhydrous nitroethane was added slowly. The temperature of the stirred reaction was kept at −78° C. for 1.5 hours and then allowed to return to room temperature overnight. Triethylamine (1 g) was added, the solution filtered and the nitroethane evaporated. A solution of the residue in 20 ml of water was treated with an excess of a saturated aqueous solution of potassium carbonate and the liberated oil separated by extraction with ethyl acetate. The ethyl acetate solution was washed several times with water before being dried over magnesium sulfate and evaporated. The residue obtained was endo-8-(3,5-dimethylbenzoyloxy)hexahydro-2,6-methano-2H-quinolizin3(4H)-one and this was treated with methylene chloride and ethereal hydrogen chloride to give crystals of the hydrochloride salt melting at about 291° C.

EXAMPLE 9

When the procedure of Example 8 is repeated using endo- hexahydro-8-hydroxy-2,6-methano-2H-quinolizin-3(4H)-one and the appropriate acid chloride, the corresponding esters listed below are obtained. As necessary, the acid chlorides are obtained from the appropriate carboxylic acids by standard procedures, for example, using thionyl chloride. To convert the ester to a corresponding acid salt, it is reacted with the appropriate acid with alternative solvents being used as desired.

endo-Hexahydro-8-(3-indolylcarbonyloxy)-2,6-methano-2H-quinolizin-3(4H)-one methanesulfonate melting at about 278° C.

endo-8-(3-Benzofurancarbonyloxy)hexahydro-2,6-methano2H-quinolizin-3(4H)-one endo-8-(3-Benzo[b]thiophenecarbonyloxy)hexahydro-2,6- methano-2H-quinolizin-3(4H)-one endo-8-(1-Benzyl-lH-indol-3-ylcarbonyloxy)hexahydro-2,6-methano-2H-quinolizin-3(4H)-one endo-Hexahydro-8-(1-methyl-1H-indol-3-ylcarbonyloxy)-2,6-methano-2H-quinolizin-3(4H)-one endo-8-(4-Bromo-2-furylcarbonyloxy)hexahydro-2,6-methano-2H-quinolizin-3(4H)-one endo-Hexahydro-8-(5-phenyl-2-furylcarbonyloxy)-2,6-methano-2H-quinolizin-3(4H)-one endo-8-(3-Chloro-2-thienylcarbonyloxy)hexahydro-2,6-methano-2H-quinolizin-3(4H)-one endo-Hexahydro-8-(5-methyl-2-thienylcarbonyloxy)-2,6-methano-2H-quinolizin-3(4H)-one endo-Hexahydro-8-(1-methyl-1H-pyrrol-2-ylcarbonyloxy)-2,6-methano-2H-quinolizin-3(4H)-one endo-8-(3-Chloro-4-nitrobenzoyloxy)hexahydro-2,6-methano-2H-quinolizin-3(4H)-one endo-8-(3-Chloro-4-dimethylaminobenzoyloxy)hexahydro2,6-methano-2H-quinolizin-3(4H)-one endo-8-(3,5-Dichlorobenzoyloxy)hexahydro-2,6-methano-2H-quinolizin-3(4H)-one endo-8-(3,5-Dimethoxybenzoyloxy)hexahydro-2,6-methano-2H-quinolizin-3(4H)-one endo-8-(2,5-Dimethylbenzoyloxy)hexahydro-2,6-methano-2H-quinolizin-3(4H)-one.

EXAMPLE 9A

When the procedure of Example 8 was repeated using 3-indolylcarbonyl chloride and crude oily endo-hexahydro-8-hydroxy-2,6-methano-2H-quinolizin-3(4H)-one (this material was obtained as described in Example 7 and contained a quantity of the exo isomer), crystals of endo-hexahydro-8-(3-indolylcarbonyloxy)-2,6-methano-2H-quinolizin-3(4H)-one methanesulfonate melting at about 278° C. were obtained after recrystallization from water. Basification of the mother liquor and chromatography of the recovered material on silica using ethyl acetate-hexane as the eluant gave exohexahydro-8-(3-indolylcarbonyloxy)-2,6-methano-2H-quinolizin-3(4H)-one melting at about 259–260° C.

EXAMPLE 10

Oxalyl chloride (0.76 ml) was slowly added to a stirred solution of 1 g of 5-methylindole in 20 ml of anhydrous ether at 0° C. The precipitate which formed was filtered off and dried at 80° C. to give 5-methyl-3-indolylglyoxylyl chloride.

A stirred solution of 205 mg of anhydrous silver tetrafluoroborate in 10 ml of anhydrous nitroethane was treated with a solution of 282.5 mg of endo-hexahydro-8-hydroxy-2,6-methano-2H-quinolizin-3(4H)-one tetrafluoroborate (obtained by treating the free amine with an equivalent of hydrofluoroboric acid) in 10 ml of anhydrous nitroethane at room temperature. A solution of 233 mg of 5-methyl-3-indolylglyoxylyl chloride in 10 ml of anhydrous nitroethane was slowly added and the mixture stirred at room temperature overnight. Triethylamine (101 mg) was added, the solution filtered and the nitroethane evaporated. A solution of the residue in 15 ml of water was treated with a saturated aqueous solution of potassium carbonate and the liberated oil separated by extraction with ethyl acetate. The ethyl acetate solution was washed several times with water before being dried over magnesium sulfate and evaporated. The residue was treated with methylene chloride and ethereal hydrogen chloride, and the solid filtered off and recrystallized from 2-propanol to give endo-hexahydro-8-(5-methyl-3-indolylcarbonyloxy)-2,6-methano-2H-quinolizin-3(4H)-one hydrochloride.

When the above procedure was repeated using the appropriate substituted indole in place of the 5-methylindole, the following compounds were obtained:

endo-Hexahydro-8-(5-chloro-3-indolylcarbonyloxy)-2,6-methano-2H-quinolizin-3(4H)-one hydrochloride melting at about 317–320° C. (with decomposition) after recrystallization from ethanol.

endo-Hexahydro-8-(5-cyano-3-indolylcarbonyloxy)-2,6-methano-2H-quinolizin-3(4H)-one hydrochloride melting at about 304–305° C. (with decomposition) after recrystallization from ethanol.

endo-Hexahydro-8-(5-methoxy-3-indolycarbonyloxy)-2,6-methano-2H-quinolizin-3(4H)-one hydrochloride melting at about 303° C. (with decomposition) after recrystallization from isopropanol.

endo-Hexahydro-8-(1-methyl-3-indolylcarbonyloxy)-2,6-methano-2H-quinolizin-3(4H)-one hydrochloride melting at about 251° C. after recrystallization from ethanol.

endo-Hexahydro-8-(6-methyl-3-indolylcarbonyloxy)-2,6-methano-2H-quinolizin-3(4H)-one oxalate melting at about 340–342° C. after recrystallization from ethanol.

Also obtained in the same way are endo-hexahydro-8-(5-carbamoyl-3-indolylcarbonyloxy)-2,6-methano-2H-quinolizin-3(4H)-one and endo-hexahydro-8-(5-hydroxy-3-indolycarbonyl-oxy)-2,6-methano-2H-quinolizin-3(4H)-one. In the later case, the staring material is 5-benzyloxyindole and the initial product is debenzylated by reduction using standard procedures.

EXAMPLE 11

Dimethylamine (40% solution in water, 0.68 g) and formaldehyde (30% solution in water, 0.49 g) were successively added to a solution of 1.25 g of endo-8-(3,5-dimethylbenzoyloxy)hexahydro-2,6-methano-2H-quinolizin-3(4H)-one in a mixture of 4 ml of ethanol and 2 ml of water. The stirred mixture was heated at 70–75° C. for 16 hours and concentrated. Toluene (50 ml) was added and the mixture evaporated at 110° C.

A solution of the residue [which contained endo-8-(3,5-dimethylbenzoyloxy)hexahydro-4-methylene-2,6-methano-2H-quinolizin-3(4H)-one] in 30 ml of ethanol was hydrogenated at room temperature and atmospheric pressure in the presence of 0.2 g of platinum oxide (Adams catalyst). One equivalent of hydrogen was absorbed in one hour. The catalyst was filtered off, the ethanol evaporated and the residue treated with one equivalent of hydrofluoroboric acid in water. Evaporation of the aqueous solution gave a crystalline residue which was recrystallized from ethanol to give endo-8-(3,5-dimethylbenzoyloxy)hexa,hydro-4-methyl-2,6-methano-2H-quinolizin-3(4H)-one tetrafluoroborate melting at about 270–275° C.

EXAMPLE 12

A solution of endo-8-(3-indolylcarbonyloxy)hexahydro-2,6-methano-2H-quinolizin-3(4H)-one (1.42 g) in ethanol (5 ml) was treated with fluoboric acid (0.64 g, 60% aqueous solution) and the mixture evaporated to give endo-8-(3-indolylcarbonyloxy)-hexahydro-2,6-methano-2H-quinolizin3(4H)-one tetrafluoroborate (1.8 g).

A stirred suspension of the above salt (1.8 g) in anhydrous nitroethane (30 ml) was treated with propane-1,3-dithiol (3 ml) and boron trifluoride etherate (3 drops) and the mixture stirred overnight at room temperature. The nitroethane was removed by evaporation and the residue triturated with ether. The solid product was filtered off, washed several times with ether, treated with water (25 ml), saturated aqueous potassium carbonate (3 ml) and ether (50 ml). The ether solution was separated off, dried ($MgSO_4$) and evaporated to give the propane dithioketal derivative, m.p. 226–229° C. (1.6 g).

Hydrazine hydrate (3 ml) was added dropwise during one hour to a stirred refluxing solution of the above dithioketal (0.5 g) in isopropanol (20 ml) in the presence of Raney nickel (6 g, previously washed three times with isopropanol). The reflux was maintained for a further 30 minutes, the hot solution filtered through a triple superphosphate, the nickel washed several times with hot isopropanol and the combined filtrates evaporated to give endo-8-(3-indolylcarbonyloxy-2,6-methanooctahydro-2H-quinolizine as the free base (50 mg). Addition of methylene chloride and ethereal hydrogen chloride gave the hydrochloride (30 mg), m.p. 311–313° C. (from ethanol).

EXAMPLE 13

The procedure of Example 12 was repeated using endohexahydro-8-hydroxy-2,6-methano-2H-quinolizin-3(4H)-one in place of the ester. The dithioketal obtained was reduced as described in the final paragraph except that the hydrazine hydrate was left out. This gave exo-octahydro-2,6-methano-2H-quinolizin-8-ol which was then reacted with 3,5-dimethylbenzoyl chloride to give exo-8-(3,5-dimethylbenzoyloxy)octahydro-2,6-methano-2H-quinolizine which was converted to the hydrochloride, m.p. 255–256° C. by standard procedures.

EXAMPLE 14

A stirred mixture of 1-methyl-3-indazolylcarboxylic acid (0.31 g), thionyl chloride (2 ml) and chloroform (10 ml) was refluxed for 2 hours and the solvent was evaporated to give a residue of 1-methyl-3-indazolylcarbonyl chloride.

A stirred solution of 395 mg of anhydrous silver tetrafluoroborate in anhydrous nitroethane (10 ml) was treated with a solution of endo-hexahydro-8-hydroxy-2,6-methano-2H-quinolizin-3(4H)-one tetrafluoroborate (475 mg) in anhydrous nitroethane (10 ml) at −78° C. A solution of 1-methyl-3-indazolylcarbonyl chloride (340 mg) in anhydrous nitroethane (5 ml) was slowly added during one hour and the reaction mixture was then allowed to warm to room temperature overnight. The mixture was poured into a saturated aqueous solution of potassium carbonate (30 ml). The mixture obtained was filtered and the separated solid was washed with ethyl acetate. The filtrate was then extracted twice with ethyl acetate (2×20 ml) and the solvent was evaporated from the combined ethyl acetate fractions. A solution of the residue in ethyl acetate (20 ml) was washed with water (3×15 ml) and dried over magnesium sulfate, and the solvent was evaporated to give a residual material. This material was purified by silica preparative plate chromatography using a mixture of ethanol/ethyl acetate (30:70) as eluant. The desired product compound, endo-hexahydro-8-(1-methyl-3-indazolylcarbonyloxy)-2,6-methano-2H-quinolizin-3(4H)-one, formed a band with an Rf 0.35 and was isolated by extraction with ethanol/ethyl acetate (50:50).

EXAMPLE 15

A stirred mixture of 690 mg of endo-hexahydro-8-(3-indolylcarbonyloxy)-2,6-methano-2H-quinolizin-3(4H)-one, 400 mg of methyl iodide, and 100 ml of acetonitrile was refluxed for 2 hours and then allowed to stand overnight at room temperature. The crystalline solid which formed was separated by filtration and dried to give endo-hexahydro-8-(3-indolylcarbonyloxy)-2,6-methano-5-methyl-3(4H)-oxo-2H-quinolizinium iodide melting at about 310–312° C. with decomposition.

EXAMPLE 16

A mixture of 1.84 g of 4-quinolinecarboxylic acid, 25 ml of methylene chloride and trifluoroacetic anhydride was stirred at room temperature for 5 minutes and then cooled to 0° C. A mixture of 1.92 g of endo-hexahydro-8-hydroxy-2,6-methano-2H-quinolizin-3(4)-one, 1.2 g of trifluoroacetic acid, 25 ml of methylene chloride and 20 ml of tetrahydrofuran was slowly added and the mixture stirred at room temperature for 20 hours. The solid present was removed by aqueous potassium carbonate. The resulting basic solution was extracted with ethyl acetate and the ethyl acetate extract was dried and filtered. The solvent was then evaporated to give residual material which was treated with ether and ethereal hydrogen chloride to give endo-hexahydro-8-(4-quinolinylcarbonyloxy)-2,6-methano-2H-quinolizin-3(4H)-one hydrochloride melting at about 302° C. (dec) after recrystallization from ethanol.

EXAMPLE 17

A solution of endo-8-(3-indolylcarbonyloxy)hexahydro-2,6-methano-2H-quinolizin-3(4H)-one (50 mg) in 1 ml of ethanol was added dropwise to 20 mg of sodium borohydride in 1 ml of ethanol at room temperature. The reaction was then quenched by the addition of 2 ml of saturated aqueous ammonium chloride solution. The aqueous mixture was extracted three times with ethyl acetate and the solvent was evaporated from the combined organic extracts under nitrogen. This gave a solid residue which was endo-8-(3-indolylcarbonyloxy)-2,6-methanooctahydro-2H-quinolizin-3-ol.

EXAMPLE 18

Oxalyl chloride (10 ml) was slowly added to a stirred solution of 11.7 g of indole in 50 ml of anhydrous ether at 0° C. The temperature was allowed to reach room temperature and the mixture stirred for a further 2 hours. The orange precipitate was filtered off, washed with anhydrous ether and dried at 50° C. to give 3-indolylglyoxylyl chloride.

A suspension of 6.42 g of silver tetrafluoroborate in 300 ml of anhydrous toluene was evaporated to dryness to give a residue of the anhydrous salt. A solution of this anhydrous salt in anhydrous nitroethane (50 ml) was slowly added to a stirred solution of 7.74 g of trans-hexahydro-8-hydroxy-2,6-methano-2H-quinolizin-3(4H)-one tetrafkyiriborate and 6 g of 3-indolylglyoxylyl chloride in 100 ml of anhydrous nitroethane cooled to −10° C. under nitrogen. The mixture was stirred overnight at room temperature, poured into a saturated aqueous solution of potassium carbonate (30 ml) and the resulting mixture was extracted with 200 ml of ethyl acetate. The separated organic phase was dried over magnesium sulfate, the solvent evaporated and the residue redissolved in 200 ml of ethyl acetate. After washing three times with water to remove unchanged starting alcohol, the ethyl acetate solution was dried and evaporated to give a residue (7.4 g) of crude trans-hexahydro-8-(3-indolylcarbonyloxy)-2,6-methano-2H-quinolizin-3(4H)-one base. The residue was treated with a solution of 2.2 g of methanesulphonic acid in 50 ml of ethanol at 60° C. The solid material remaining undissolved was filtered off and the reddish-brown solution was treated with charcoal. On cooling, the filtered solution afforded crystals of trans-hexahydro-8-(3-indolylcarbonyloxy)-2,6-methano-2H-quinolizin-3(4H)-one methanesulphonate monohydrate (66%).

What is claimed is:

1. A compound of the formula:

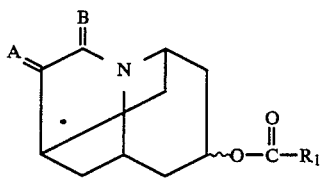

wherein the two lines to both A and B indicate a double bond to a single group or two single bonds to two individual groups as specified; A is (H)(H), =O, (H)(OH) or =N—OH; B is (H)(H), (H)(CH$_3$), (H)(CH$_2$NR$_3$R$_4$) or =CH$_2$ wherein R$_3$ and R$_4$ are C$_{2-4}$ alkyl or are combined to give tetramethylene, pentamethylene or —CH$_2$CH$_2$—O—CH$_2$CH$_2$—; R$_1$ is

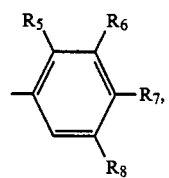

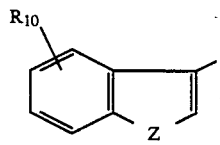

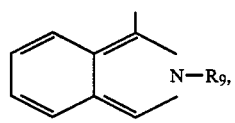

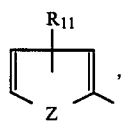

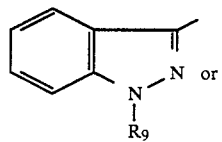

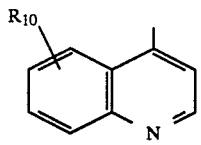

wherein Z is NR$_9$, O or S; R$_5$; R$_6$ and R$_8$ are each hydrogen, halogen, C$_{1-3}$ alkyl or C$_{1-3}$ alkoxy; R$_7$ is hydrogen, amino, (C$_{1-4}$ alkyl)amino, (C$_{1-4}$ alkyl)$_2$ amino, C$_{1-3}$ alkoxy or nitro; R$_9$ is hydrogen, C$_{1-4}$ alkyl or phenyl(C$_{1-2}$ alkyl); R$_{10}$ is hydrogen, halogen, C$_{1-4}$ alkyl, C$_{1-4}$ alkoxy, hydroxy, cyano or —CONH$_2$; R$_{11}$ is hydrogen, halogen, C$_{1-4}$ alkyl or phenyl; the wavy line indicates that the configuration of the oxygen substituent on the ring can be endo or exo; and the pharmaceutically acceptable acid addition and quaternary ammonium salts of the aforesaid compounds.

2. A compound according to claim 1 which has the formula:

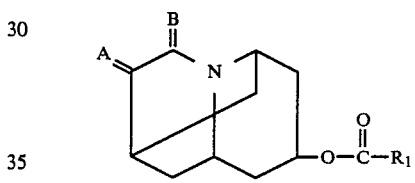

wherein the two lines to both A and B indicate a double bond to a single group or two single bonds to two individual groups as specified; A is (H)(H), =O, (H)(OH) or =N—OH; B is (H)(H), (H)(CH$_3$), (H)(CH$_2$NR$_3$R$_4$) or =CH$_2$ wherein R$_3$ and R$_4$ are C$_{2-4}$ alkyl or are combined to give tetramethylene, pentamethylene or —CH$_2$CH$_2$—O—CH$_2$CH$_2$—; R$_1$ is

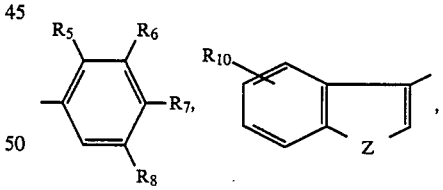

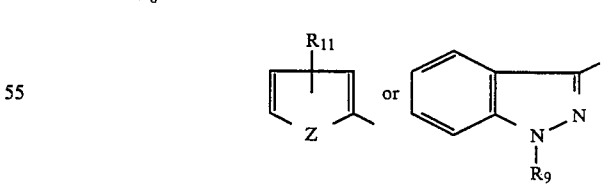

wherein Z is NR$_9$, O or S; R$_5$, R$_6$ and R$_8$ are each hydrogen, halogen, C-$_{1-3}$ alkyl or C$_{1-3}$ alkoxy; R$_7$ is hydrogen, amino, (C$_{1-4}$ alkyl)amino, (C$_{1-4}$ alkyl)$_2$amino, C$_{1-3}$ alkoxy or nitro; R$_9$ is hydrogen, C$_{1-4}$ alkyl or phenyl(C$_{1-2}$ alkyl); R$_{10}$ is hydrogen, halogen, C$_{1-4}$ alkyl, C$_{1-4}$ alkoxy, hydroxy, cyano or —CONH$_2$; R$_{11}$ is hydrogen, halogen, C$_{1-4}$ alkyl or phenyl; and the pharmaceutically acceptable acid addition and quaternary ammonium salts of the aforesaid compounds.

3. A compound according to claim 1 which has the formula:

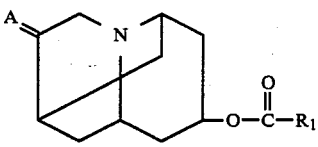

wherein the two lines to A indicate a double bond to a single group or two single bonds to two individual groups as specified; A is (H)(H), =O, (H)(OH) or =N—OH; $R_1$ is

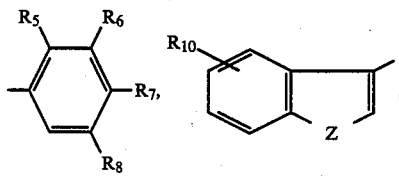

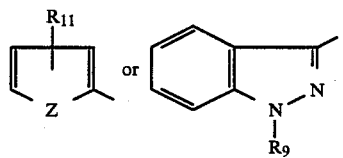

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, $(C_{1-4}$ alkyl)amino, $(C_{1-4}$ alkyl)$_2$amino, $C_{1-3}$ alkoxy or nitro; $R_9$ is hydrogen, $C_{1-4}$ alkyl or phenyl $(C_{1-2}$ alkyl); $R_{10}$ is hydrogen, halogen, $C_{1-4}$ alkyl, $C_{1-4}$ alkoxy, hydroxy, cyano or —$CONH_2$; $R_{11}$ is hydrogen, halogen, $C_{1-4}$ alkyl or phenyl, and the pharmaceutically acceptable acid addition and quaternary ammonium salts of the aforesaid compounds.

4. A compound according to claim 1 which has the formula:

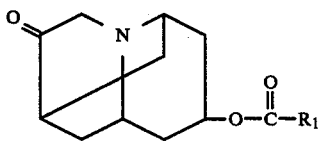

wherein $R_1$ is

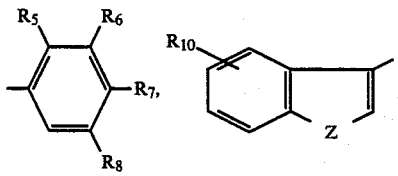

-continued

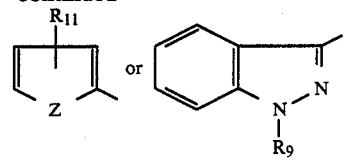

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino $(C_{1-4}$ alkyl)amino, $(C_{1-4}$ alkyl)$_2$amino, $C_{1-3}$ alkoxy or nitro; $R_9$ is hydrogen, $C_{1-4}$ alkyl or phenyl$(C_{1-2}$ alkyl); $R_{10}$ is hydrogen, halogen, $C_{1-4}$ alkyl, $C_{1-4}$ alkoxy, hydroxy, cyano or —$CONH_2$; $R_{11}$ is hydrogen, halogen, $C_{1-4}$ alkyl or phenyl, and the pharmaceutically acceptable acid addition and quaternary ammonium salts of the aforesaid compounds.

5. A compound according to claim 1 which has the formula:

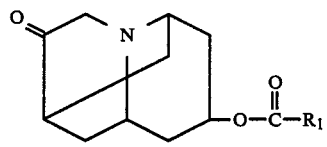

wherein $R_1$ is

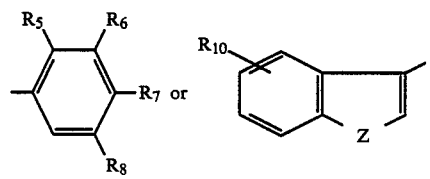

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, $(C_{1-4}$ alkyl)amino, $(C_{1-4}$ alkyl)$_2$amino, $C_{1-3}$ alkoxy or nitro; $R_9$ is hydrogen, $C_{1-4}$ alkyl or phenyl$(C_{1-2}$ alkyl(1 $R_{10}$ is hydrogen, halogen, $C_{1-4}$ alkyl, $C_{1-4}$ alkoxy, hydroxy, cyano or —$CONH_2$, and the pharmaceutically acceptable acid addition and quaternary ammonium salts of the aforesaid compounds.

6. A compound according to claim 1 which is endo-8-(3,5-dimethylbenzoyloxy) hexahydro-2,6-methano-2H-quinolizin-3(4H)-one.

7. A compound according to claim 1 which is endohexahydro-8-(3-indolylcarbonyloxy)-2,6-methano-2H-quinolizin-3(4H)-one.

8. A compound according to claim 1 which is endo-hexahydro-8-(1-methyl-3-indazolylcarbonyloxy)-2,6-methano-2H-quinolizin-3(4H)-one.

9. Endo-Hexahydro-8hydroxy-2,6-methano-2H-quinolizin-3(4H)-one.

10. A compound according to claim 1 which is exo-hexahydro-8-(3-indolylcarbonyloxy)-2,6-methano-2H-quinolizin-3(4H)-one.

* * * * *

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 4,906,755 |
| ISSUED | : | March 6, 1990 |
| INVENTOR | : | Maurice W. Gittos |
| PATENT OWNER | : | Hoechst Marion Roussel, Inc. |
| PRODUCT | : | ANZEMET® (doloasetron mesylate) |

This is to certify that an application under 35 U.S.C. § 156 has been filed in the U.S. Patent and Trademark Office, requesting extension of the term of U.S. Patent No. 4,906,755 based upon the regulatory review of the product ANZEMET® (doloasetron mesylate) by the Food and Drug Administration. Since it appears that the requirements of the law have been met, this certificate extends the term of the patent for the period of 1,579 days from March 6, 2007, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 19th day of January 2001.

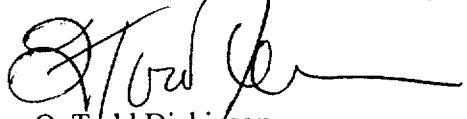

Q. Todd Dickinson
Under Secretary of Commerce for Intellectual Property and
Director of the United States Patent and Trademark Office